United States Patent [19]

Hasson

[11] Patent Number: 5,318,578
[45] Date of Patent: Jun. 7, 1994

[54] APPARATUS FOR DELIVERING A SUTURE INTO A BODY CAVITY AND METHOD OF USING THE APPARATUS

[75] Inventor: Harrith M. Hasson, 2043 N. Sedgwick, Chicago, Ill. 60614

[73] Assignee: Harrith M. Hasson, Chicago, Ill.

[21] Appl. No.: 852,772

[22] Filed: Mar. 17, 1992

[51] Int. Cl.$^5$ .............................. A61B 17/00
[52] U.S. Cl. ........................ 606/139; 606/144; 606/147; 606/148; 606/228; 606/232
[58] Field of Search ............. 606/139, 144, 147, 148, 606/151, 111, 112

[56] References Cited

U.S. PATENT DOCUMENTS

| | | | |
|---|---|---|---|
| 2,455,833 | 12/1948 | Trombetta | 606/139 |
| 3,687,138 | 8/1972 | Jarvik | 606/139 |
| 3,763,860 | 10/1973 | Clarke | 123/830 |
| 3,878,848 | 4/1975 | Hiebert | 606/148 |
| 4,489,732 | 12/1984 | Hasson . | |
| 4,635,638 | 1/1987 | Weintraub | 606/147 |
| 4,760,848 | 8/1988 | Hasson | 606/222 |
| 5,037,433 | 8/1991 | Wilk et al. | 606/144 |
| 5,059,201 | 10/1991 | Asnis | 606/148 |
| 5,100,421 | 3/1992 | Christoudias | 606/147 |
| 5,129,912 | 7/1992 | Noda et al. | 606/139 |
| 5,152,769 | 10/1992 | Baber | 606/139 |
| 5,196,022 | 3/1993 | Bilweis | 606/139 |

FOREIGN PATENT DOCUMENTS 1561963  5/1990  U.S.S.R. .............................. 606/144

Primary Examiner—Stephen C. Pellegrino
Assistant Examiner—Jeffrey A. Schmidt
Attorney, Agent, or Firm—Wood, Phillips, VanSanten, Hoffman & Ertel

[57] ABSTRACT

An instrument for delivering a pre-tied suture assembly, having a needle carrying a thread with a noose thereon, into a body cavity. The needle has a pointed free end to puncture a tissue and guide movement of the needle and thread therethrough. The instrument has an elongate body with proximal and distal ends. Structure is provided on the body for holding the needle in a transfer position with the pointed free end of the needle shielded to prevent inadvertent puncture of a tissue as the suture assembly is introduced into a body cavity through the instrument. The body has a noose receiving portion to be surrounded by the noose with the needle in its transfer position to prevent the noose from closing upon itself. There is first structure on the elongate body for a) preventing a noose on the noose receiving portion from sliding from the noose receiving portion off of the distal free end of the body with the first structure in a first position and b) allowing a noose to slide from the noose receiving portion off of the distal free end of the body with the first structure in a second position.

32 Claims, 6 Drawing Sheets

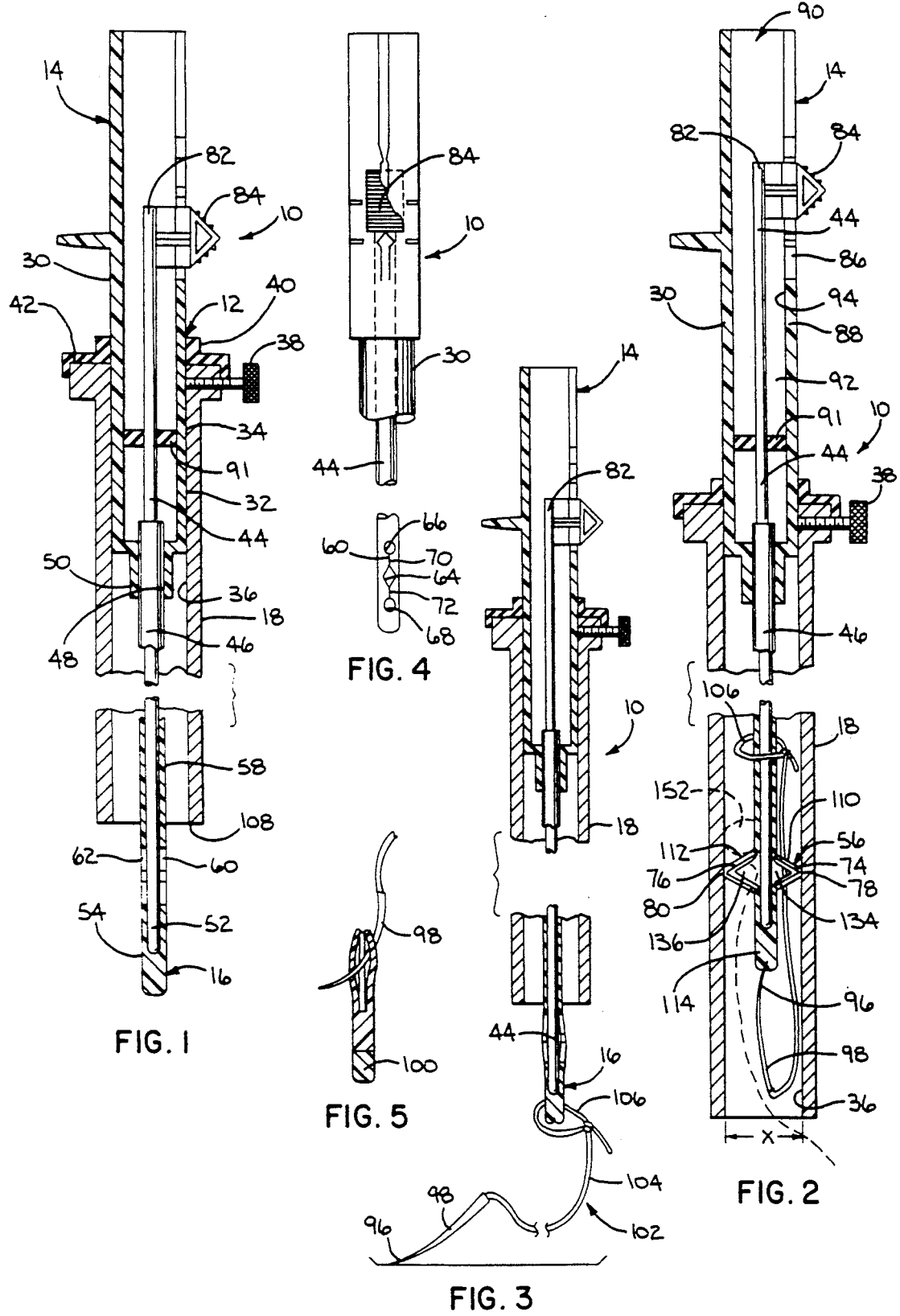

5,318,578

APPARATUS FOR DELIVERING A SUTURE INTO A BODY CAVITY AND METHOD OF USING THE APPARATUS

BACKGROUND OF THE INVENTION

1. Field of the Invention

This invention relates to surgical suturing procedures and, more particularly, to a device for delivering a pre-tied suture assembly into a body cavity, as during a laparoscopic procedure. The device can also be utilized to assist needle transfer and repositioning during suturing. The invention is further directed to a method of a) delivering a suture into a cavity using the inventive structure and b) assisting the suture tying process.

2. Background Art

Various techniques are known for delivering sutures into a body cavity during laparoscopy. By one method, a conventional forceps is utilized. If the user grabs the needle on the suture with the forceps jaws and draws the suture in a trailing direction, there is a risk that the exposed part of the needle may snag as it is being introduced to the body cavity or, alternatively, that the rigidly held needle may puncture an organ within the cavity, once introduced thereinto.

Alternatively, the user can grip the suture thread and pull the needle through in a trailing direction. While this obviates the problem of organ puncture, it introduces an additional problem. A substantial force must be applied by the jaws of the forceps on the thread to draw the needle into the cavity without fear of the suture's dislodging from the forceps. The gripping action of the jaws on the suture may cause fraying of the suture or a localized weakening which could result in a failure of the suture during the tying process.

It is also known to pre-tie a loop in a suture before the suture and needle are introduced into a body cavity. This loop acts as a noose to facilitate the tying of the first knot by the user. The loop/noose diameter is diminished by drawing on the suture thread while holding any part of the noose/loop stationary. If the pre-tied suture is introduced to a body cavity by grasping the suture, other than at the loop/noose and by drawing the suture structure into the cavity, as with a forceps, there is a tendency of the loop/noose diameter to diminish and possibly completely close, which is obviously undesirable.

The above problems would still be encountered if one were to surround the trailing body of a forceps with the loop/noose and grasp the thread and/or needle with the forceps forwardly thereof in directing the suture into the body cavity. If the loop/noose is drawn too tightly around the forceps body, the user would have to work the loop/noose loose to free the suture from the instrument once the same is in the body cavity. If the loop/noose is too large, it could slide uncontrollably along the forceps body and over the jaws thereon during introduction to prematurely separate entirely from the instrument.

A still further problem encountered in suturing during laparoscopy is that of manipulating the suturing needle once the suture is within the cavity. Various instruments have been devised for positively gripping a needle and for allowing the needle to be driven through adjacent tissue edges to initiate a knot, which is cinched to close an incision. Once the first instrument drives the needle through the tissue, the needle must be released, repositioned and resituated in that same instrument. In the transition between the gripping and re-gripping of the needle, the needle may dangle freely from the suture protruding from the tissue. By one technique, the user can use the same instrument to try to re-grip the needle. The difficulties with this are aggravated by the lack of suitable instruments available to readily accomplish this. One known instrument, for example, has a slot on one side thereof in which the needle must be located to effect holding thereof. The user must often blindly try to guide the dangling needle into that opening, which can be very inconvenient and time consuming.

Alternatively, a forceps-type instrument can be introduced into the body cavity solely for the purpose of holding the needle in a transition position and assisting the relocation of the needle in the device which is used to drive it through the tissue. The difficulty with this is that proper orientation of the needle is seldom achieved with the use of existing instruments, which often require gripping and regripping of the needle several times until proper orientation of the needle in the needle driver is obtained. Further, the user may be required to constantly remove and insert different instruments as various procedures are being performed.

SUMMARY OF THE INVENTION

The present invention is specifically directed to overcoming the above enumerated problems in a novel and simple manner.

According to the invention, an instrument is provided for delivering a pre-tied suture assembly, having a needle carrying a thread with a noose thereon, into a body cavity. The needle has a pointed free end to puncture a tissue and guide movement of the needle and thread therethrough. The instrument has an elongate body with proximal and distal ends. Structure is provided on the body for holding the needle in a transfer position with the pointed free end of the needle shielded to prevent inadvertent puncture of a tissue as the suture assembly is introduced into a body cavity through the instrument. The body has a noose receiving portion to be surrounded by the noose with the needle in its transfer position to prevent the noose from closing upon itself. There is first structure on the elongate body for a) preventing a noose on the noose receiving portion from sliding from the noose receiving portion off of the distal free end of the body with the first structure in a first position and b) allowing a noose to slide from the noose receiving portion off of the distal free end of the body with the first structure in a second position.

With the inventive structure, a pre-tied suture assembly can be readily introduced to a body cavity without fear of puncturing a patient's organ and without altering the effective noose diameter. It should be noted that it is not necessary that the noose actually be constrictable as the structure can function equally effectively with a noose having a fixed diameter.

In one form, the needle holding structure is adjacent to the distal free end of the body. In one preferred form, the holding structure is a pad of material which is penetrable by the pointed free end of a needle. For example, the pad can be made from compressible material such as rubber.

In one form, the noose receiving portion of the body has an outer surface with a first diameter and the first structure is a blocking shoulder that has a diameter that is greater than the first diameter with the first structure in its first position. In one preferred form, the instrument body has a lengthwise axis and the first structure consists of first and second blocking shoulders located at diametrically opposite positions relative to the instrument body axis.

For convenience of operation, the first structure can be moved between its first and second positions by an actuator that is remote from the first structure. In one form, a slidable actuator is used to place the first structure selectively in its first and second positions.

The invention also contemplates the combination of the instrument with a pre-tied noose assembly.

The invention further contemplates the above instrument in combination with a sleeve defining a passageway to be placed in communication with a cavity in which a suturing procedure is to be performed. There is cooperating structure on the proximal end of the body and sleeve for blocking free communication of air between a cavity through the sleeve passageway to externally of the passageway so as to confine a gas commonly used to distend a working cavity during laparoscopy.

Structure can be provided to fix the sleeve and instrument selectively in a plurality of different operative relationships.

In one form, the elongate body has an internal stem and an external sleeve with a cylindrical outer surface defining the noose receiving portion. There is a cut in the sleeve which is connected to the stem. The stem and sleeve can selectively be placed in first and second relative positions. The external sleeve is radially bulged at the cut with the stem and sleeve in their first relative position to define a blocking shoulder to prevent a noose surrounding the external sleeve from sliding over and past the free distal end of the elongate body. With the stem and external sleeve in their second relative position, the external sleeve section, that is bulged radially outwardly with the stem and sleeve in their first relative position, and internal stem are sufficiently close to each other to captively hold a suturing needle therebetween. This latter feature, in addition to allowing a suture noose to be slipped off of the instrument body, also allows the sleeve and stem to cooperatively be used to accept and capture a needle to hold the same internally of a body cavity. This obviates the need to have to pull the inventive instrument out and substitute therefor a forceps-type instrument to assist the exchange of a needle as a suturing process is carried out, which process generally involves repetitively gripping a needle, directing the needle through a tissue, releasing the needle and re-gripping the needle.

The invention further contemplates an instrument with an elongate body having a proximal end and a free distal end, structure for holding a needle in a transfer position as the suture assembly held by the instrument is introduced into a body cavity, a noose receiving portion to be surrounded by a noose with the needle in its transfer position to prevent the noose from completing closing upon itself, and first structure, separate from the needle holding structure, for a) preventing a noose on the noose receiving portion from sliding off of the noose receiving portion with the first structure in a first position and b) allowing a noose to slide from the noose receiving portion off of the instrument with the first structure in a second position.

The invention further contemplates a method of delivering a pre-tied suture assembly, including a needle and suture, using an instrument such as that described above. A noose of a pre-tied suture assembly is extended around the noose-receiving portion of the instrument body. The first structure is placed in a first position to maintain the noose on the noose receiving portion while the instrument is directed into a cavity into which suturing is to be performed. Once the suture is introduced, the first structure can be placed in a second position and the noose slid off of the noose receiving portion.

To prevent needle hang up and possible puncture of internal organs, the inventive method further contemplates holding the needle with the instrument before introducing the suture assembly into a cavity.

The suture holding step preferably consists of the step of penetrating a part of the instrument with the pointed free needle end so that the sharp needle end is shielded.

The invention further contemplates an instrument for delivering a suture assembly, having a needle carrying a thread, which instrument has an elongate body with a proximal end and a distal end and resilient structure adjacent to the distal end of the body to be penetrated by the pointed free end of a needle on a suture assembly to thereby hold the needle in a transfer position with the pointed free end of the needle shielded to prevent inadvertent puncture of a tissue as the suture assembly is introduced into a body cavity through the instrument.

The elongate body can be made in whole or in part from the resilient material defining the resilient structure adjacent to the distal end of the body. Alternatively, the elongate body can be made from a first material and the resilient structure made as a pad from a second material that is separately attached to the elongate body.

The invention further contemplates the instrument in combination with a suture assembly. In one form, the distal body end is a free end, the resilient structure is provided adjacent to the distal free end of the body, and first structure is provided on the body for selectively a) preventing a portion of the thread on a suture assembly with the needle on a suture assembly in its transfer position from passing in a first direction from the proximal end of the body towards the distal end of the body past the free end of the body with the first structure in its first position and b) allowing the thread portion to pass in the first direction beyond the free distal end of the body with the first structure in a second position.

The invention also contemplates the instrument in combination with a sleeve having an inside surface defining a passageway through which the instrument can be directed, with the sleeve surface defining a first diameter. The first structure, in its first position, defines a blocking shoulder in the sleeve passageway to prevent passage thereby of the portion of the thread.

The invention also contemplates the combination of the instrument with a suture assembly wherein the thread portion on the suture assembly has an enlargement to abut the blocking shoulder on the body with the first structure in its first position. The enlargement may be a knot, integrally formed with the thread, an enlarged thread, such as a bead, clip, staple, or the like, attached to the thread, or other suitable structure that provides an effectively enlarged portion on the thread to abut the first shoulder.

Alternatively, a pre-formed/pre-tied noose surrounds a portion of the body and abuts the shoulder on the first structure with the first structure in its first position.

The invention further contemplates an instrument having an elongate body with proximal and distal ends, structure on the body for holding the needle in the transfer position so that the suture assembly can be introduced into a body cavity by directing the distal body end into a body cavity with the thread on the suture assembly in a trailing position, and first structure on the body for preventing a portion of the thread on a suture assembly from passing in a first direction from the proximal end of the body toward the distal end of the body past the first structure with the first structure in a first position and b) allowing the thread portion to pass in the first direction beyond the distal end of the body with the first structure in a second position.

BRIEF DESCRIPTION OF THE DRAWINGS

FIG. 1 is a cross-sectional view of an instrument for introducing a suture assembly into a cavity according to the present invention;

FIG. 2 is a cross-sectional view of the inventive instrument as in FIG. 1 and showing a suture assembly mounted to the instrument with the instrument in a first mode for directing the suture assembly into a body cavity;

FIG. 3 is a view as in FIG. 2 with the instrument in a second mode in which the suture assembly is shown being released from the instrument;

FIG. 4 is a fragmentary elevation view of an actuator for changing the instrument between the first and second modes of FIGS. 2 and 3 on one end of the instrument and showing the distal end of the instrument in a suture release/needle gripping position;

FIG. 5 is a fragmentary sectional view of the distal end of the instrument shown gripping a needle as to effect transportation thereof;

DETAILED DESCRIPTION OF THE DRAWINGS

Figure 6:
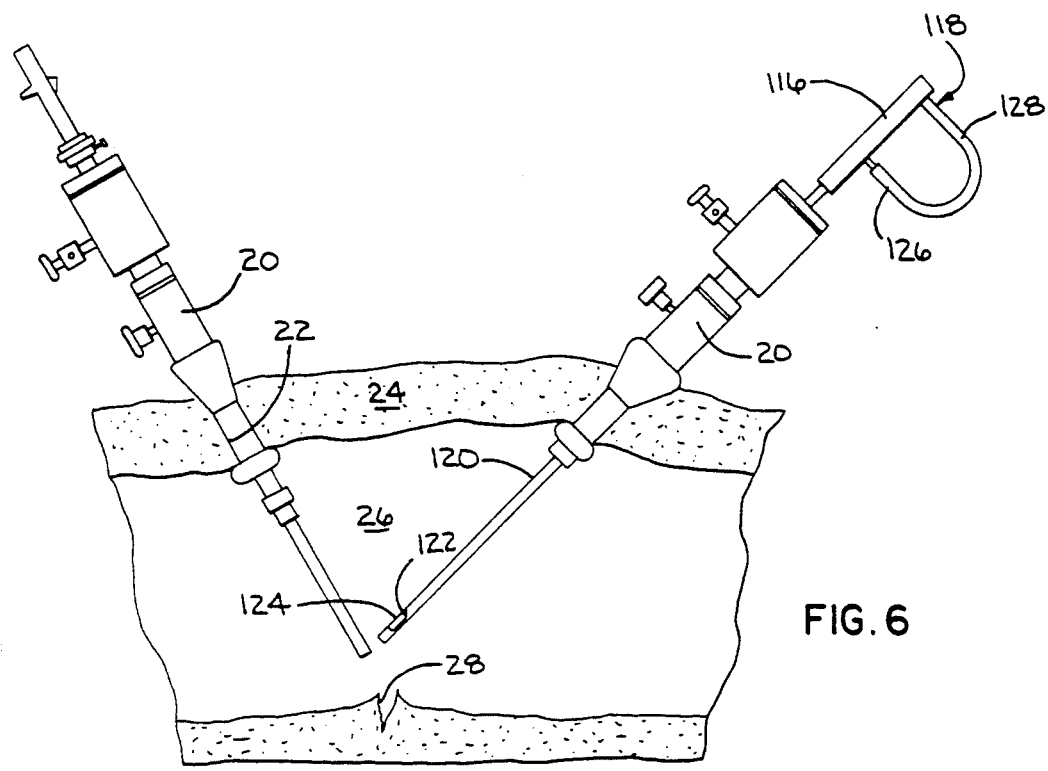
FIG. 6 is a schematic representation of a body cavity having an organ with an incision therein and showing the inventive instrument, on the left in FIG. 6, in cooperative relationship with a separate instrument/device for gripping a needle and manipulating the needle by directing the needle forcibly through tissue to be sutured.

In FIGS. 1-4, a preferred form of instrument for delivering a pre-tied suture assembly, according to the present invention, is shown at 10. The instrument 10 has an elongate body 12 with a proximal end 14 and a distal end 16. The body 12 resides within a concentric sleeve 18 which may itself be guided directly through an incision or, alternatively, into an instrument support 20 (FIG. 6), which is shown directed through an incision 22 in tissue 24 bounding a body cavity 26 having an internal incision 28 to be sutured.

The body 12 has a foundation section 30 with a cylindrical, stepped, outer surface 32 with a larger diameter portion 34 thereof closely received within a mating through passageway 36 defined internally of the sleeve 18. A releasable set screw 38 is provided to selectively fix the desired relative position between the foundation section 30 and sleeve 18. A gasket 40 maintains the seal at the juncture of the foundation section 30 and sleeve 18 at the upper/proximal end 42 of the sleeve 18.

The body 12 includes an operating stem 44 surrounded by an outer sleeve 46, which conforms to and is fixedly secured within a bore 48 in a reduced diameter portion 50 of the foundation section 30. The free distal end 52 of the stem 44 is fixedly secured to the outer sleeve 46. Upward movement of the stem 44 draws the distal sleeve end 54 upwardly to effect radial bulging of the sleeve 46, as shown at 56 in FIG. 2, to increase the effective diameter of the outer surface 58 of the sleeve 46.

This bulging is facilitated by providing lengthwise slits 60, 62 at diametrically opposite locations on the sleeve 46. More particularly, to facilitate controlled radial expansion/bulging of the sleeve 46, the slits 60, 62 are configured as the exemplary slit 60 shown in FIG. 4. The slit 60 has a central diamond shaped cut-out 64 and circular cut-outs 66, 68 axially above and below the cut-out 64. The cut-outs 64, 66 are interconnected by a straight cut 70, while the cut-outs 64, 68 are interconnected by a straight cut 72. The cut-outs 64, 66, 68 are dimensioned and spaced so that as the stem 44 is drawn upwardly, the outer sleeve 46 radially expands to produce diametrically opposite, radially inwardly opening, V-shaped wings 74, 76, with the radially outermost edges 78, 80 respectively thereof spaced from each other a distance approximately equal to the diameter X of the sleeve passageway 36.

The proximal end 82 of the stem 44 has an external, knurled actuator 84 which moves guidingly in a lengthwise slot 86 defined through the wall 88 of the foundation section 30. To prevent escape of air from the passageway 36 to externally of the instrument 10, as through the slot 86 or the open end 90 of the foundation section 30, a gasket 91 is provided and fills the annular space 92 between the stem 44 and inside surface 94 of the foundation section 30. The gasket 90 is fixed to only one of the foundation section 30 and stem 44 to allow sliding movement of the stem 44 through the actuator 84 relative to the foundation section 30.

The free distal end 16 of the body 12 is made from a soft, compressible material, such as rubber, which is readily penetrable yet which will firmly embrace the pointed free end 96 of a conventional suturing needle 98. The entire body 12 can be made entirely from a material, such as rubber or, alternatively, an end fitting 100 (FIG. 5) can be separately attached to allow construction of the remainder of the body 12 from any desired material.

A principal objective of the above instrument is to conveniently introduce a pre-tied suture assembly as at 102 into a body cavity 26 (FIG. 6). The suture assembly 102 consists of the aforementioned needle 98 which is connected to a suture/thread 104 which has at its end a loop 106 which may be pre-formed/pre-tied to a fixed diameter or made in the form of a constrictable noose, with the latter being preferred and described herein in connection with the preferred embodiment of the invention. The operation of the device will now be described below with reference to FIGS. 6–13 which show the sequence of tying a suture using the inventive instrument 10.

The set screw 38 is released to allow the sleeve 18 to be slid upwardly on the foundation section 30 to the FIG. 1 position in which the distal end 16 of the body 12 is exposed beneath the bottom end 108 of the sleeve 18. The noose 106 is then slid over the distal end 16 of the body 12 and slid upwardly to approximately the position it occupies in FIG. 2. The outer surface 58 of the sleeve 46 serves as a noose receiving portion on the body 12 and prevents the loop/noose 106 from completely closing upon itself during manipulation of the suture assembly 102. The actuator 84 is then pushed upwardly to reposition the stem 44 so as to expand the wings 74, 76 to the position shown in FIG. 2. In the FIG. 2 position, the wings 74, 76 define blocking shoulders 110, 112, respectively, which prevent the noose 106 from sliding downwardly past and beyond the distal end 16 of the body 12.

The free needle end 96 is then pressed into the tip 114 at the free distal end 16 of the body 12, as shown in FIG. 2. The material of the tip 114, or the separate tip end fitting 100 is sufficiently compressible to allow insertion of the needle 98 and rigid enough to maintain the needle in a substantially fixed orientation. After the needle 98 is placed in its holding or transfer position of FIG. 2, the sleeve 18 can be slid back downwardly relative to the foundation section 30 and locked through the set screw 38 in that position, to protect the distal end 16 of the body 12 and to shield diameter or made in the form of a constrictable noose, with the latter being preferred and described herein in connection with the preferred embodiment of the invention. The operation of the device will now be described below with reference to FIGS. 6–13 which show the sequence of tying a suture using the inventive instrument 10.

The set screw 38 is released to allow the sleeve 18 to be slid upwardly on the foundation section 30 to the FIG. 1 position in which the distal end 16 of the body 12 is exposed beneath the bottom end 108 of the sleeve 18. The noose 106 is then slid over the distal end 16 of the body 12 and slid upwardly to approximately the position it occupies in FIG. 2. The outer surface 58 of the sleeve 46 serves as a noose receiving portion on the body 12 and prevents the loop/noose 106 from completely closing upon itself during manipulation of the suture assembly 102. The actuator 84 is then pushed upwardly to reposition the stem 44 so as to expand the wings 74, 76 to the position shown in FIG. 2. In the FIG. 2 position, the wings 74, 76 define blocking shoulders 110, 112, respectively, which prevent the noose 106 from sliding downwardly past and beyond the distal end 16 of the body 12.

The free needle end 96 is then pressed into the tip 114 at the free distal end 16 of the body 12, as shown in FIG. 2. The material of the tip 114, or the separate tip end fitting 100 is sufficiently compressible to allow insertion of the needle 98 and rigid enough to maintain the needle in a substantially fixed orientation. After the needle 98 is placed in its holding or transfer position of FIG. 2, the sleeve 18 can be slid back downwardly relative to the foundation section 30 and locked through the set screw 38 in that position, to protect the distal end 16 of the body 12 and to shield the needle 98 during introduction of the instrument 10 into the body cavity. The entire instrument 10 can then be passed directly through the incision 22 or, as shown in FIG. 6, through the instrument 20 which provides a stable support on the tissue 24 and a through passageway for the instrument 10. A suitable support instrument 20 is known to those skilled in the art. Various such instruments have been developed by the inventor herein. Once such instrument is shown in U.S. Pat. No. 5,002,557, incorporated herein by reference. Consequently, the details of the instrument 20 are omitted from the discussion herein.

A similar instrument 20 is provided through the tissue 24 to accept a needle holding/gripping and manipulating device 116. A suitable needle manipulating device, and that shown in the drawings herein, is currently being manufactured and sold by Cook Urological, a Cook Group Company and identified as its "Endoscopic Curved Needle Driver". The device 116 generally consists of a graspable handle section 118 which also serves as an actuator at a distal end thereof. The instrument 116 has an elongate body 120 with a slot 122 therein for reception of the needle 98. A camming element 124 is selectively withdrawn and biased forwardly by the handle/actuator 118 and, in the latter position, positively wedges a needle in the slot 122. The slot 122 is opened by drawing one arm 126 of the gripping section/actuator towards a stationary rear arm 126, which thereby retracts the camming element 124. Once the needle 98 is positioned in the slot 122 and the handle 118 released, the arm 126 is biased forcibly away from the other arm 128 to urge the camming element 124 forwardly to positively capture the needle 98.

Figure 7:
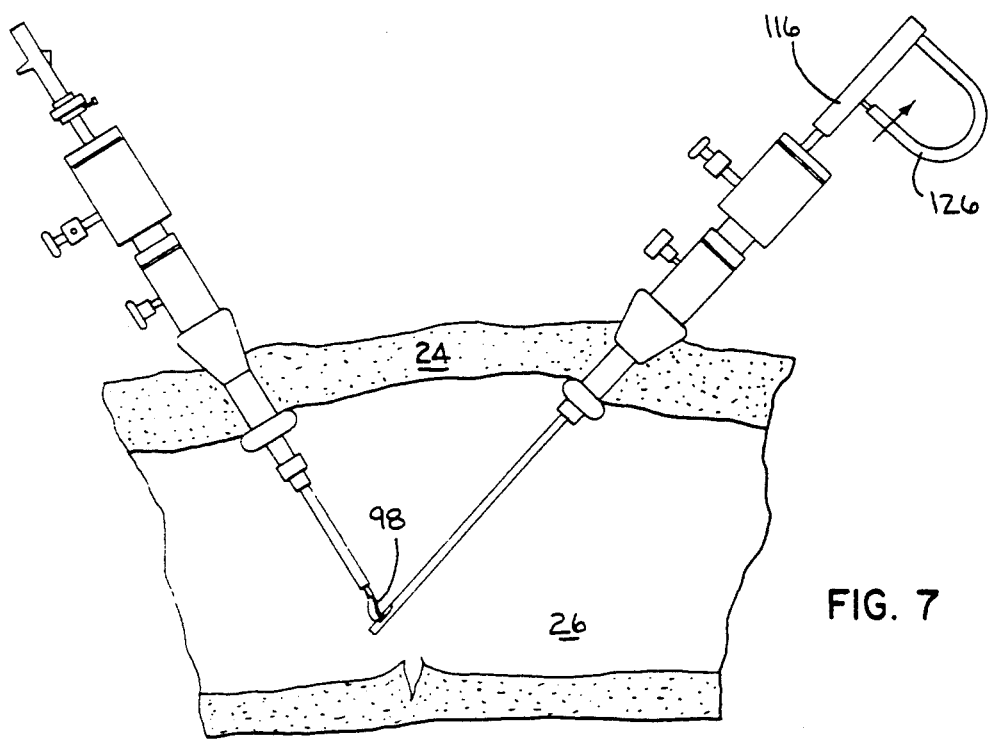
FIG. 7 is a view as in FIG. 6 showing the inventive instrument directing a pre-tied suture assembly into the body cavity for placement on the needle manipulating instrument.
Figure 8:
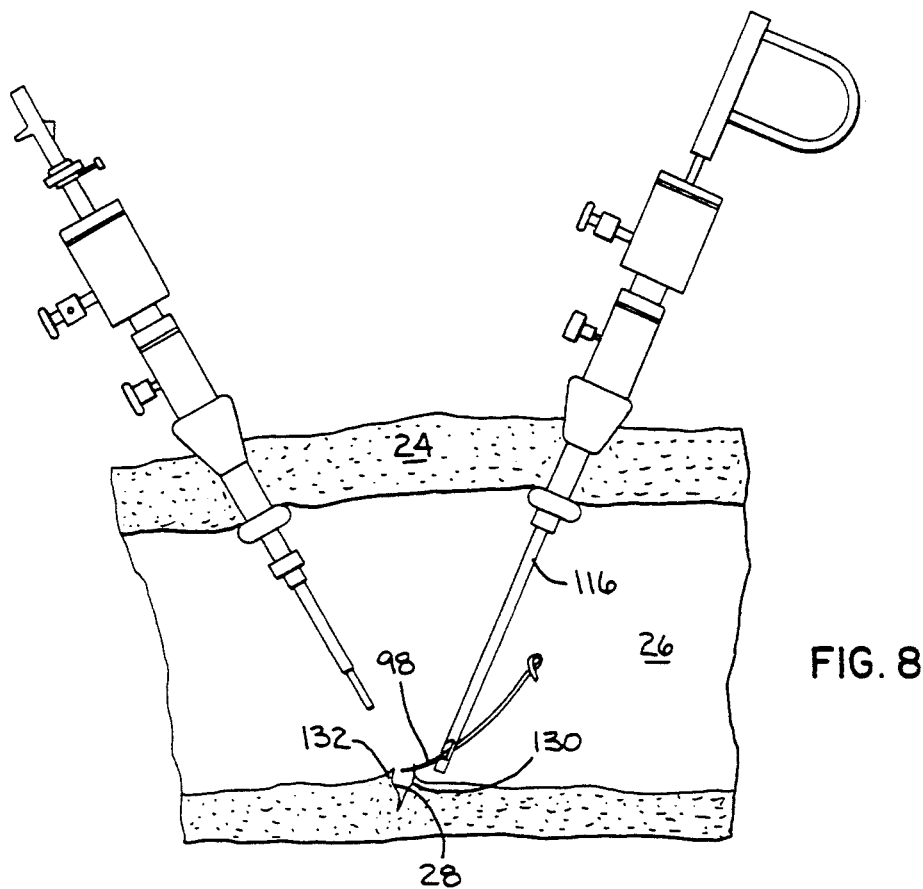
FIG. 8 shows the needle manipulating instrument directing the needle gripped thereby through tissue bounding an incision.
Figure 9:
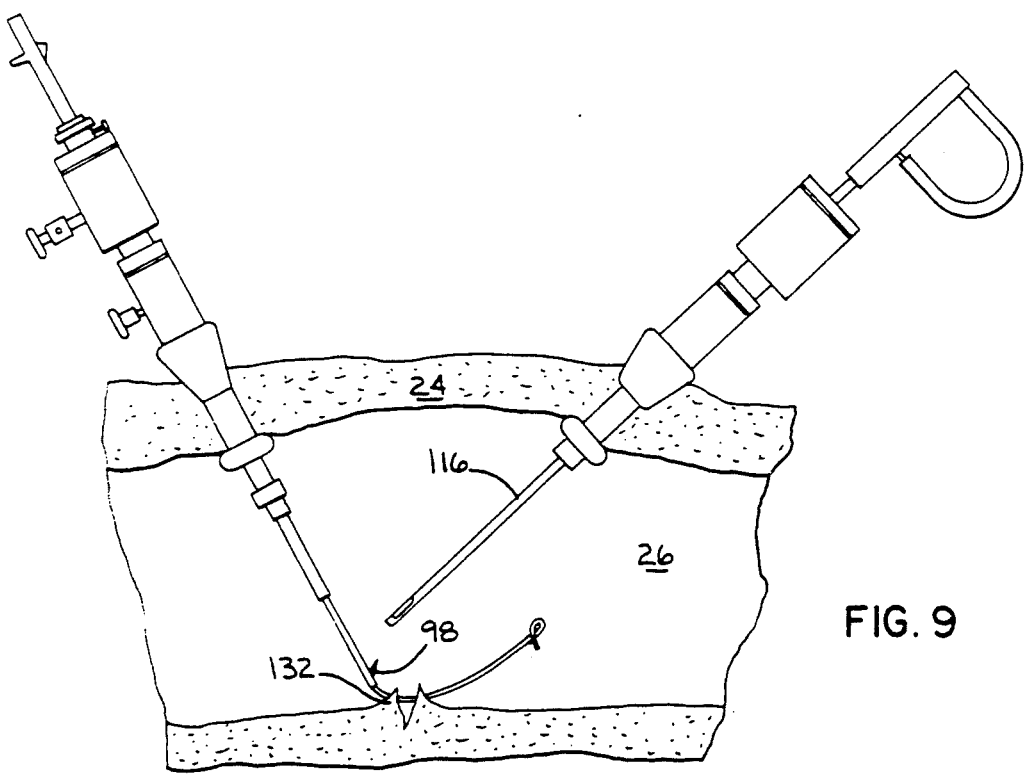
FIG. 9 shows the inventive instrument picking up the needle after the needle is passed through the tissue bounding the incision.

The instrument 10 is directed through the support instrument 20 in its FIG. 2 orientation in the vicinity of the incision 28, as shown in FIG. 6. The set screw 38 is then released to allow the body 12 to be advanced downwardly into the FIG. 1 position relative to the sleeve 18. The needle 98 is then conveniently exposed to be picked up by the needle manipulating device 116, as seen in FIG. 7. Once the needle 98 is positively grasped by the device 116, the stem 44 on the body 12 is moved through the actuator 84 from the FIG. 2 position back to the FIG. 1 position, which allows the noose 106 to be slid off of the body 12 and the suture assembly 102 to be separated entirely from the instrument 10. Through the needle manipulating device 116, the needle 98 is directed through tissue parts 130, 132 on opposite sides of the incision 28. Once the needle 98 is extended fully through the tissue part 132, it will be supported only by the suture/thread 104.

Another aspect of the invention is the ability to pick the needle 98 up conveniently with the instrument 10. Not only is this conveniently done with the instrument 10, but it obviates the need to remove the instrument 10 and insert a forceps-type instrument to pick up the needle 98 and reinsert it into the device 116 for re-gripping thereby. More particularly, the wings 74, 76 on the sleeve 46, when collapsed radially inwardly, can be used to captively hold the needle 98 against the stem 44. The instrument can thus be used to maintain the needle 98 in a transition position. To accomplish this, the wings 74, 76 are expanded as in FIG. 2 to define openings 134, 136 through which the needle 98 can be readily directed. By collapsing the wings 74, 76 through operation of the actuator 84, the needle 98 is frictionally held between one of the wings 74, 76 and the stem 44. This pickup procedure is demonstrated in FIG. 9. Alternatively, the needle 98 can be directed into the tip 114 of the body 12 or the end fitting 100 to grip and maintain the needle 98 in its transition position.

Figure 10:
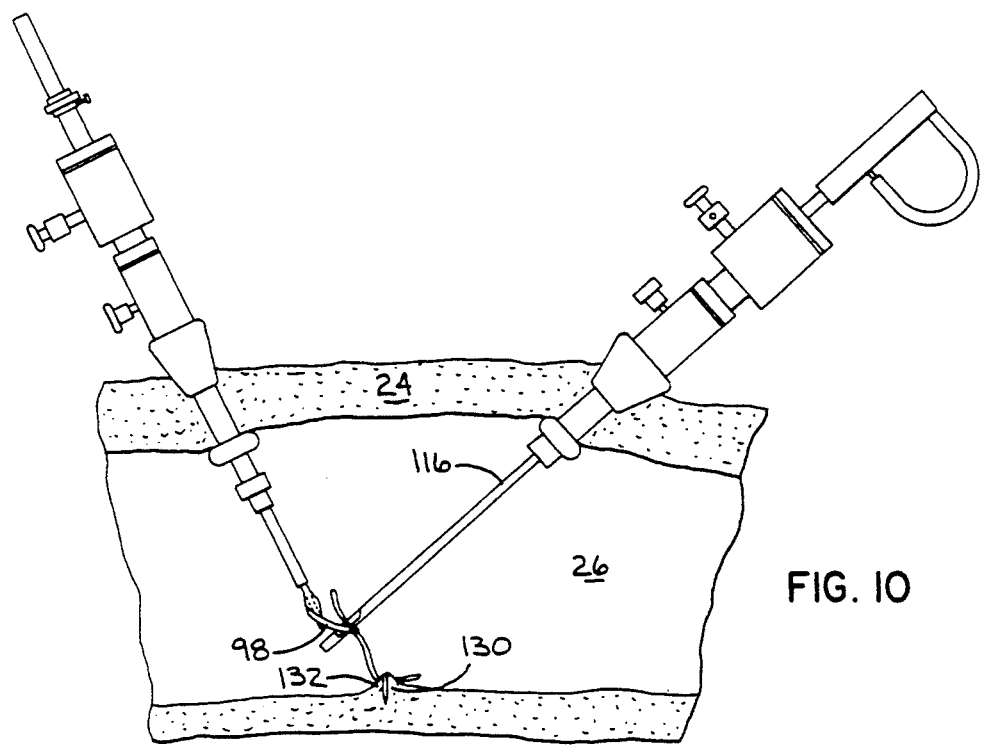
FIG. 10 shows the needle being transferred to the needle manipulation instrument for re-gripping thereby.
Figure 11:
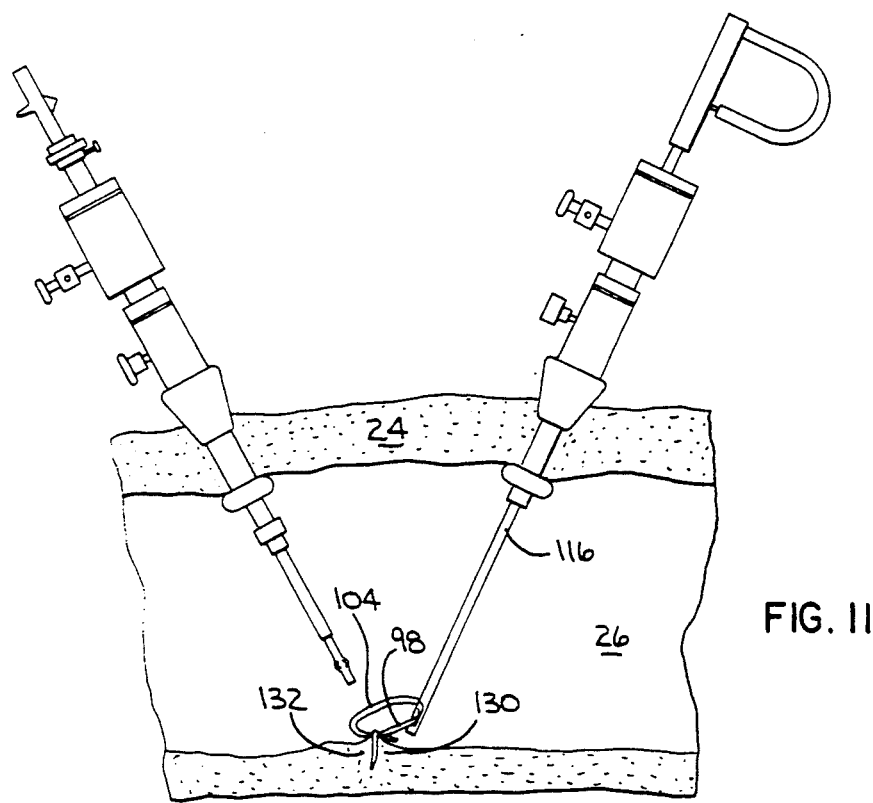
FIG. 11 shows the needle manipulating instrument being utilized to complete the suturing operation at the incision.
Figure 12:
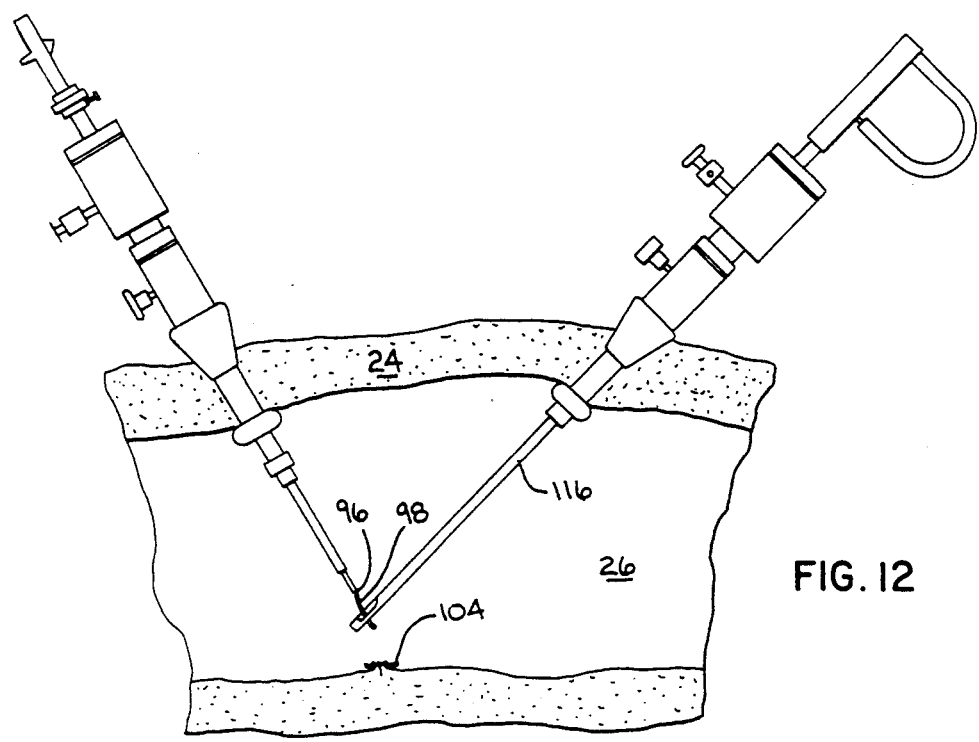
FIG. 12 shows the needle manipulating instrument placing the needle back into a holding/transfer position on the inventive instrument.
Figure 13:
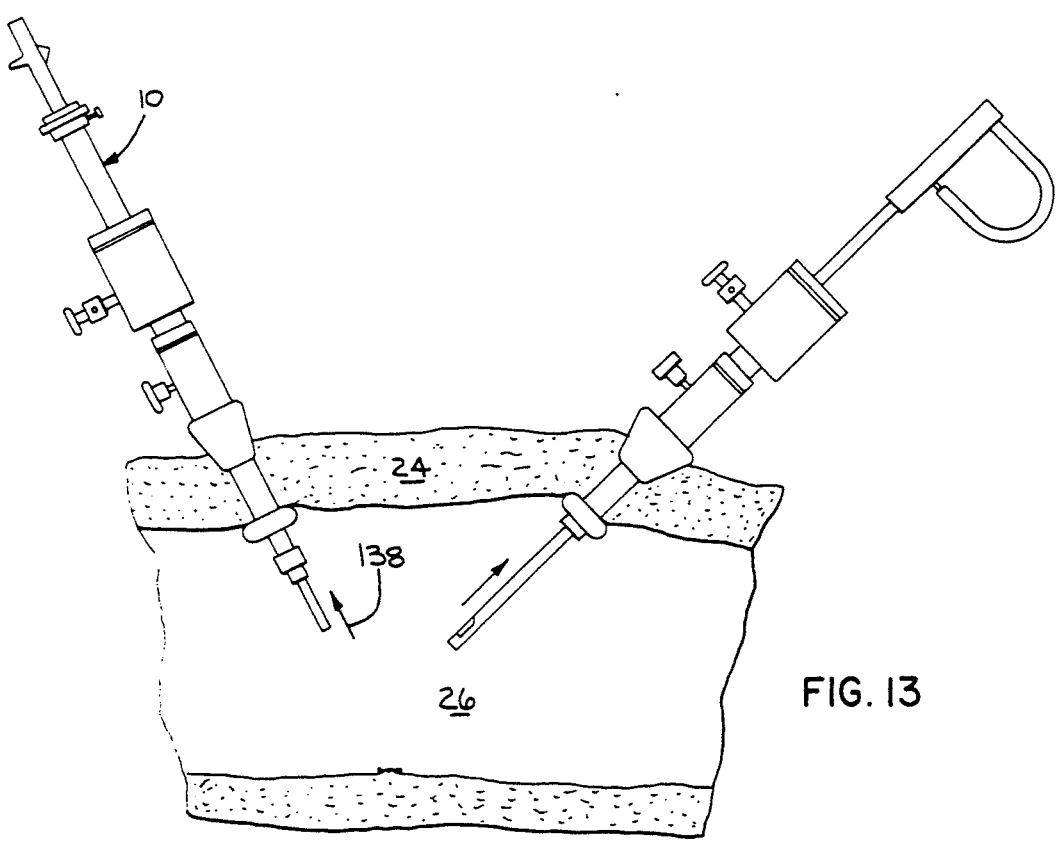
FIG. 13 shows the inventive instrument withdrawing the needle from the cavity.

In FIG. 10, the needle 98 is transferred in a desired orientation back to the device 116 to be regripped thereby to allow the needle 98 to be directed through the noose 106 to effect the first tying step. Proper orientation of the needle for regripping by he device 116 is easily achieved by simple rotation of the instrument 10. The needle 98 is then redirected by the device 116 through the tissue portions 130, 132. After the requisite number of passes of the thread 104 around the tissue parts 130, 132, the suture is tied and cut as shown in FIG. 12, to complete the suturing operation. The device 116, with the needle 98 held thereby, can then be used to press the free needle end 96 into the tip 114 of the body 12 whereupon the instrument 10 can be retracted in the direction of arrow 138 out of the cavity 26, as shown in FIG. 13.

Figure 14:
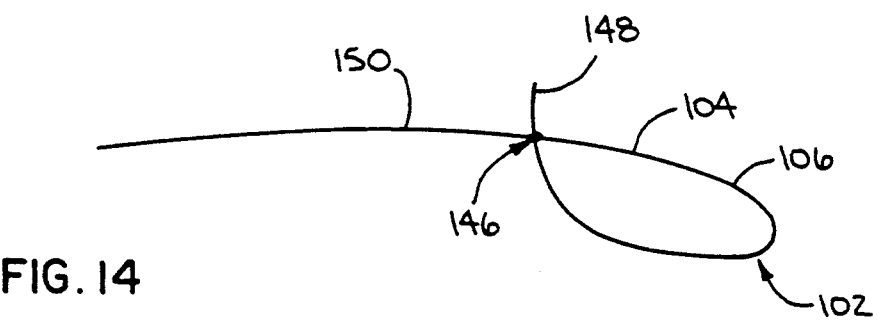
FIG. 14 is a sectional view of a suture tying thread with a pre-formed/pre-tied noose formed therein.
Figure 15:
FIG. 15 is a sectional view of a suture tying thread with an enlarged bead attached to the end thereof.
Figure 16:
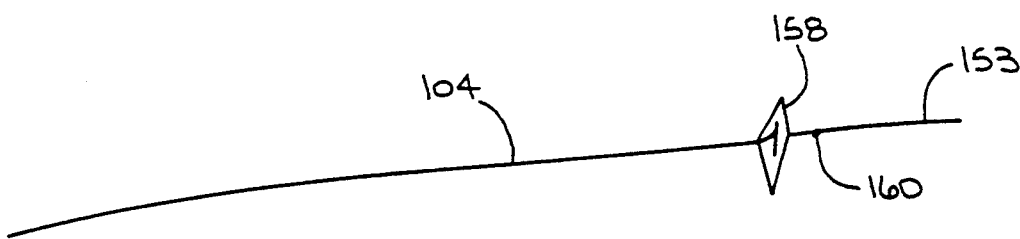
FIG. 16 is a sectional view of a suture tying thread with a clip or staple attached thereon and blocked by a knot formed in the thread.

In FIGS. 14-16, various different arrangements are shown for pre-tied/pre-formed suture assemblies. In FIG. 14, the loop/noose 106, previously described, is shown formed in the thread 104 on the suture assembly 102. An overhand knot, or the like, is shown at 146 to allow the short end 148 of the thread 104 to be held while drawing on the long end 150, to thereby constrict the diameter of the loop/noose 106.

In FIG. 15, the thread 104 is shown to have an enlargement/bead 152 attached at its trailing free end 153. The bead 152 can take any of a number of different shapes. The spherical bead shown in FIG. 15 is exemplary of but one shape that is suitable for the enlargement/bead 152. The enlargement/bead 152 has a through bore 154 for the thread 104, which can be projected through and knotted as at 156 to prevent the enlargement/bead 152 from being drawn off of the free end 153 of the thread 104. Alternatively, the enlargement/bead 152 could be crimped onto the thread 104, or otherwise suitably held.

As seen in FIG. 2, in phantom, with the needle 98 penetrating the tip 114 in a transfer position therefor, the enlargement/bead 152 is drawn by the thread 104 through the sleeve 18 in a trailing direction. The enlargement/bead 152 substitutes for the loop/noose 106 and, as seen in FIG. 2, abuts one of the blocking shoulders 110, 112 to prevent passage over and past the distal end 16 of the body 12. Consequently, the enlargement/bead 152 accomplishes the same end as the loop/noose 106.

Figure 17:
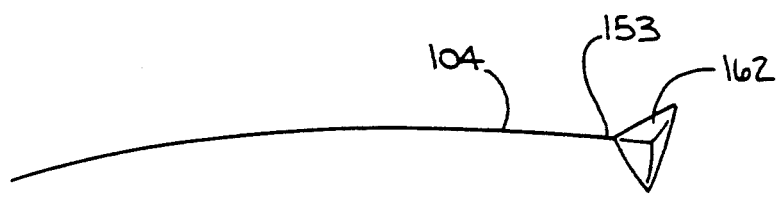
FIG. 17 is a sectional view of a suture tying thread with an enlarged element on the end thereof which has an alternative configuration to the bead and clip/staple shown in FIGS. 15 and 16.

In FIGS. 16 and 17, alternatives to the enlargement/bead 152 are shown. In FIG. 16, a clip 158 is shown crimped onto the thread 104. The crimping can be sufficient to hold the clip 158 stationary. Alternatively, the crimping may be sufficient just to hold the clip 158 onto the thread 104 so that it is slidable lengthwise thereof. A knot 160, or other suitable structure can then be used to confine the shifting of the grip 158 off the free end 153 of the thread 104.

In FIG. 17, an enlarged body 162 is shown as a multi-sided geometric figure to demonstrate one additional potential configuration of structure that can be used to block passage of a trailing portion, and in most instances the free end 153 of the thread 104, over and past the distal end 16 of the body 12.

It can be seen that the pre-formed/pre-tied suture 102 can be conveniently introduced into the body cavity 26 without undesirably altering the diameter of the loop/noose 106 at the distal suture end as might interfere with the suture formation and without the needle 98 hanging up during this process or potentially puncturing any organ internally of the cavity 26. Withdrawal of the needle 98 is accomplished in like fashion. At the same time, the instrument 10 serves the dual purpose of holding the needle 98 in a transition position to allow release and re-gripping of the needle 98 during the suturing process. This obviates the need for removal of the instrument 10 and insertion of a forceps-type instrument in its place to hold the needle 98 in the transition position. At the same time, the instrument 10 is particularly effective in that the suture/thread 104 is never squeezed as might cause it to fray or develop a localized weakening point which might precipitate its failure.

The foregoing disclosure of specific embodiments is intended to be illustrative of the broad concepts comprehended by the invention.

I claim:

1. In combination:
   a) a pre-tied suture assembly having a needle carrying a thread with a noose thereon; and
   b) an instrument for delivering the pre-tied suture assembly into a body cavity, said instrument comprising:
      an elongate body having a proximal end and a free distal end;
      means on the body for holding the needle in a transfer position with the pointed free end of the needle shielded to prevent inadvertent puncture of a tissue as the suture assembly is introduced into a body cavity,
      said elongate body having a noose receiving portion to be surrounded by the noose with the needle in its transfer position to prevent the noose from closing upon itself; and
      first means on the elongate body for a) preventing the noose on the noose receiving portion from sliding from the noose receiving portion off of the distal free end of the body with the first means in a first position and b) allowing the noose to slide from the noose receiving portion off of the distal free end of the body with the first means in a second position.

2. The combination according to claim 1 wherein the holding means is adjacent to the distal end of the body, the noose receiving portion has an outer surface with a first diameter and the first means comprises a blocking shoulder that has an effective diameter that is greater than the first diameter with the first means in its first position.

3. The combination according to claim 2 wherein said instrument body has a lengthwise axis and the first means comprises first and second blocking shoulders at diametrically opposite locations relative to the instrument body axis.

4. The combination according to claim 1 wherein the holding means comprises a pad of material which can be penetrated by the pointed free end of the needle of the pre-tied suture assembly.

5. The combination according to claim 4 wherein the pad material is compressible rubber.

6. The combination according to claim 1 wherein actuator means are provided on said instrument body at a location remote from said first means for selectively placing the first means in its first and second positions.

7. The combination according to claim 1 further in combination with a sleeve with a passageway to be placed in communication with a cavity in which a suturing procedure is to be performed, and cooperating means on the proximal end of the elongate body and sleeve for blocking free communication of air between a cavity through the sleeve passageway to externally of the passageway.

8. The combination according to claim 7 including means for releasably fixing the relative positions of the sleeve and instrument for delivering a pre-tied noose assembly.

9. The combination according to claim 1 wherein said elongate body has an internal stem and an external sleeve with a cylindrical outer surface defining the noose receiving portion, there being a cut in the sleeve, and said first means includes cooperating means, interconnecting the body stem and sleeve, for placing the stem and external sleeve selectively in first and second relative positions, said external sleeve bulged at the cut with the stem and sleeve in said first relative position to define a bulged external sleeve section defining a blocking shoulder to prevent the noose surrounding the external sleeve from sliding over the blocking shoulder and over and past the free distal end of the elongate body.

10. The combination according to claim 9 wherein with the stem and external sleeve in their second relative position, the bulged external sleeve section and stem are sufficiently close to each other to captively hold a suturing needle therebetween.

11. The combination according to claim 1 wherein the elongate body and holding means are made entirely from plastic.

12. An instrument for delivering a pre-tied suture assembly into a body cavity, said suture assembly having a needle carrying a thread with a noose formed by the thread, the needle having a pointed free end to puncture a tissue and guide movement of the needle and thread therethrough, said instrument comprising:
an elongate body having a proximal end and a free distal end;
means for holding a needle in a transfer position as a suture assembly held by the instrument is introduced into a body cavity;
a noose receiving portion to be surrounded by a noose with a needle in its transfer position to prevent a noose from completely closing upon itself; and
first means separate from the holding means for a) preventing a noose on the noose receiving portion from sliding off of the noose receiving portion with the first means in a first position and b) allowing a noose to slide from the noose receiving portion off of the instrument with the first means in a second position,
wherein the holding means comprises a discrete pad of material attached at the free distal end of the body which pad is made of a different material than that of the body and can be penetrated by the pointed free end of a needle on a pre-tied suture assembly,
wherein the pad does not extend from the free distal end of the body toward the proximal end of the body as far as the holding means.

13. The instrument for delivering a pre-tied noose assembly according to claim 12 wherein the holding means is adjacent to the distal end of the body, the noose receiving portion has an outer surface with a first diameter and the first means comprises a blocking shoulder that has an effective diameter that is greater than the first diameter with the first means in its first position.

14. The instrument for delivering a pre-tied noose assembly according to claim 12 wherein actuator means are provided on said instrument body at a location remote from said first means for selectively placing the first means in its first and second positions.

15. An instrument for delivering a pre-tied suture assembly into a body cavity, said suture assembly having a needle carrying a thread with a noose formed by the thread, the needle having a pointed free end to puncture a tissue and guide movement of the needle and thread therethrough, said instrument comprising:
an elongate body having a proximal end and a free distal end;
means for holding a needle in a transfer position as a suture assembly held by the instrument is introduced into a body cavity;
a noose receiving portion to be surrounded by a noose with a needle in its transfer position to prevent a noose from completely closing upon itself;
first means separate from the holding means for a) preventing a noose on the noose receiving portion from sliding off of the noose receiving portion with the first means in a first position and b) allowing a noose to slide from the noose receiving portion off of the instrument with the first means in a second position,
wherein the holding means comprises a discrete pad of material attached to the body which pad is made of a different material than that of the body and can be penetrated by the pointed free end of a needle on a pre-tied suture assembly; and
a pre-tied suture assembly comprising a needle with a pointed free end and carrying a thread with a noose thereon to surround the noose receiving portion.

16. The instrument for delivering a pre-tied noose assembly according to claim 15 wherein the pad material is compressible rubber.

17. An instrument for delivering a pre-tied suture assembly into a body cavity, said suture assembly having a needle carrying a thread with a noose formed by the thread, the needle having a pointed free end to puncture a tissue and guide movement of the needle and thread therethrough, said instrument comprising:
an elongate body having a proximal end and a free distal end;
means for holding a needle in a transfer position as a suture assembly held by the instrument is introduced into a body cavity;
a noose receiving portion to be surrounded by a noose with a needle in its transfer position to prevent a noose from completely closing upon itself;
first means separate from the holding means for a) preventing a noose on the noose receiving portion from sliding off of the noose receiving portion with the first means in a first position and b) allowing a noose to slide from the noose receiving portion off of the instrument with the first means in a second position, wherein the holding means comprises a discrete pad of material attached to the body which pad is made of a different material than that of the body and can be penetrated by the pointed free end of a needle on a pre-tied suture assembly, wherein said elongate body has an internal stem and an external sleeve with a cylindrical outer surface defining the noose receiving portion, there being a cut in the sleeve, and said first means includes cooperating means, interconnecting the body stem and sleeve, for placing the stem and external sleeve selectively in first and second relative positions, said external sleeve bulged at the cut with the stem and sleeve in said first relative position to define a bulged external sleeve section defining a blocking shoulder to prevent a noose surrounding the external sleeve from sliding over the blocking shoulder and over and past the free distal end of the elongate body.

18. The instrument for delivering a pre-tied noose assembly according to claim 17 wherein with the stem and external sleeve in their second relative position, the bulged external sleeve section and stem are sufficiently close to each other to captively hold a suturing needle therebetween.

19. An instrument for delivering a needle through a tissue opening into a body cavity, said instrument comprising:

an elongate body having a proximal end and a distal end; and resilient means on, and adjacent to the distal end of, the body to be penetrated by the pointed free end of a needle on a suture assembly to thereby positively hold the needle in a transfer position to prevent inadvertent puncture of a tissue as the suture assembly is introduced into a body cavity, there being in combination with said instrument a suture assembly with a needle having a pointed free end for penetrating the resilient means and a thread carried by the needle, there further being means on the body for releasably holding the thread on the body, wherein the distal body end is a free end, the resilient means is provided adjacent to the distal free end of the body and first means are provided on the body for selectively a) preventing a portion of the thread on the suture assembly, with the needle on the suture assembly in its transfer position, from passing in a first direction from the proximal end of the body toward the distal end of the body, past the free end of the body with the first means in a first position and b) allowing the thread portion to pass in the first direction beyond the free distal end of the body with the first means in a second position.

20. The instrument for delivering a suture assembly according to claim 19 in combination with a sleeve having an inside surface defining a passageway through which the instrument can be directed, said sleeve surface defining a first diameter, said first means defining a blocking shoulder in said sleeve passageway with the first means in its first position to prevent passage thereby of said portion of the thread.

21. The instrument for delivering a suture assembly according to claim 20 wherein the thread portion has an enlargement to abut the blocking shoulder on the body with the first means in its first position to thereby prevent passage of the thread portion.

22. The instrument for delivering a suture assembly according to claim 21 wherein the enlargement comprises a body that is attached to the thread.

23. The instrument for delivering a suture assembly according to claim 20 wherein the suture portion comprises a preformed/pre-tied noose that surrounds the body and abuts the shoulder on the first means with the first means in its first position.

24. In combination:
a) a suture assembly having a needle carrying a thread, the needle having a pointed free end to puncture a tissue and guide movement of the needle and thread therethrough; and
b) an instrument for delivering the pre-tied suture assembly into a body cavity, said instrument comprising:

an elongate body having a proximal end and a distal end;

means on the body for holing the needle in a transfer position so that the suture assembly can be introduced into a body cavity by directing the distal body end into a body cavity with the thread on the suture assembly in a trailing position;

first means on the body for a) preventing a portion of the thread on the suture assembly from passing in a first direction from the proximal end of the body toward the distal end of the body past the first means with the first means in a first position and b) allowing the thread portion to pass in the first direction beyond the distal end of the body with the first means in a second position.

25. The combination according to claim 24 including a sleeve having a surface defining a through passageway for said instrument, said through passageway having a first diameter and the first means defines a blocking shoulder within said passageway, with the first means in its first position, to reduce the effective diameter of said through passageway.

26. The combination according to claim 25 wherein the thread portion has an enlargement thereon to abut the blocking shoulder on the body with the first means in its first position.

27. The combination according to claim 26 wherein the enlargement is at least one of a bead, a clip, and a staple.

28. The combination according to claim 27 wherein there is a knot in the thread to keep the at least one of the bead, clip and staple from sliding relative to the thread in at least one direction.

29. The combination according to claim 25 wherein the thread portion comprises a noose which surrounds a portion of the elongate body between the proximal and distal ends thereof and abuts the blocking shoulder on the body with the first means in its first position.

30. A method of delivering a pre-tried suture assembly into a body cavity, said method comprising the steps of:

providing a pre-tied suture assembly having a needle carrying thread with a noose thereon;

providing an instrument with a proximal end and a distal free end, an elongate body with a noose receiving portion and first means on the elongate body for a) preventing the noose on the noose receiving portion from sliding from the noose receiving portion off of the distal free end of the body with the first means in a first position and b) allowing the noose to slide from the noose receiving portion off of the distal free end of the body with the first means in a second position;

placing the noose around the noose receiving portion of the elongate instrument body;

placing the first means in its first position;

directing the instrument into a cavity into which suturing is to be performed;

placing the first means in its second position; and sliding the noose off of the noose receiving portion.

31. The method of delivering a pre-tied suture assembly according to claim 30 including the step of holding the needle with the instrument before introducing the suture assembly into a cavity.

32. The method of delivering a pre-tied suture assembly according to claim 31 wherein the needle holding step comprises the step of penetrating a part of the instrument with the pointed free needle end before introducing the suture assembly into a body cavity to prevent puncturing of an organ by the pointed free needle end as the suture assembly is introduced into a body cavity.

* * * * *